United States Patent [19]

Levinson et al.

[11] 4,193,941
[45] Mar. 18, 1980

[54] 1,1,1-TRIHALO-2-HYDROXY-4-(2-HYDROXYPHENYL)-4-BUTANONES

[75] Inventors: Sidney H. Levinson, Philadelphia; Wilford L. Mendelson, King of Prussia, both of Pa.

[73] Assignee: SmithKline Corporation, Philadelphia, Pa.

[21] Appl. No.: 948,731

[22] Filed: Oct. 5, 1978

Related U.S. Application Data

[63] Continuation-in-part of Ser. No. 843,371, Oct. 19, 1977, Pat. No. 4,152,517.

[51] Int. Cl.² ............................................. C07C 49/82
[52] U.S. Cl. ..................................................... 260/592
[58] Field of Search ........................................ 260/592

[56] References Cited

U.S. PATENT DOCUMENTS 3,627,847  12/1971  Langhammerer .................. 568/811

FOREIGN PATENT DOCUMENTS 49-124005  11/1974  Japan ........................................ 260/592

OTHER PUBLICATIONS

Dorai et al., Ind. J. Chem., vol. 13, pp. 854–855, (1975).

*Primary Examiner*—James H. Reamer
*Attorney, Agent, or Firm*—William H. Edgerton

[57] ABSTRACT

A new synthesis for the preparation of 6-(2-hydrophenyl)-3-pyridazinones whose key reaction is cyclizing a 1,1,1-trihalo-2-hydroxy-4-(2-hydroxyphenyl)-4-butanone with hydrazine. 6-(2-Hydroxyphenyl)-3-pyridazinones are important intermediates for preparing medicinally active compounds especially 3-[2-(3-tert.-butylamino-2-hydroxypropoxy)phenyl]-6-hydrazinopyridazine or its nontoxic acid addition salts. The invention claimed here is the trihalocarbinol intermediates.

3 Claims, No Drawings

1,1,1-TRIHALO-2-HYDROXY-4-(2-HYDROXY-PHENYL)-4-BUTANONES

This is a continuation-in-part application of Ser. No. 843,371 filed Oct. 19, 1977 now U.S. Pat. No. 4,152,517.

The new process of this invention for preparing 6-(2-hydroxyphenyl)-3-pyridazinones comprises the reaction of 1,1,1-trichloro-2-hydroxy-4-(2-hydroxyphenyl)-4-butanones with hydrazine at elevated temperatures in an inert organic solvent.

PRIOR ART 6-(2-Hydroxyphenyl)-3-pyridazinones are important intermediates for preparing medically active compounds. As one example, one may use these intermediates for preparing the hypotensive agent, 3-[2-(3-t-butylamino-2-hydroxypropoxy)-phenyl]-6-hydrazinopyridazine. Such 3-pyridazinone intermediates can be prepared by cyclizing the appropriate 3-benzoylpropionate ester with hydrazine followed by oxidation of the resulting phenyldihydropyridazinone appropriately protected or by reaction of an appropriate 3-benzoyl acrylic acid ester with hydrazine. Y. Y. Lee et al., *J. Korean Chemical Society* 17, 25 (1973) reported on the preparation of substituted 2,6-diphenyl-3-pyridazinones by reacting the corresponding trichloroethylideneacetophenones with phenylhydrazine. Of course, as stated, this gives the undersirable 2-phenyl-3-pyridazinone derivative. Lee reports, however, that only the pyrazoline derivative was obtained using hydrazine in place of phenylhydrazine. The present invention goes against the teaching of the art. Also pertinent to the presently claimed invention is F. G. Baddar et al., J. Chem. Soc. 3342: (1965) which discloses a number of 6-aryl-2,3-dihydropyridazin-3-ones which lack the essential hydroxyphenyl moiety.

We have now found that 1,1,1-trihalo-2-hydroxy-4-(2-hydroxyphenyl)-4-butanones (I, trihalocarbinols) react with hydrazine preferably in the presence of an elevated temperature to give the desired 6-(2-hydroxyphenyl)-3-pyridazinones (III) in good yields.

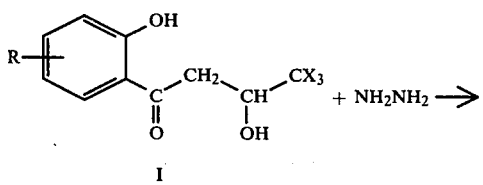

I

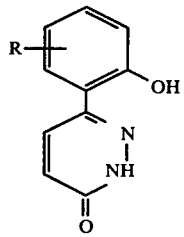

In the above exemplary sequence R may be hydrogen or any chemically inert substituent such as lower alkyl for example methyl or ethyl, lower alkoxy for example methoxy or ethoxy, lower alkylthio for example methylthio or ethylthio, halo for example fluoro, chloro or bromo or trifluoromethyl; X is bromo or preferably chloro.

Unexpectedly therefore the presence of a hydroxy substituent in the 2-position of the phenyl ring is compounds I above has been found critical to the reaction. When this hydroxy is absent or etherified as in a methoxy group, the reaction to form a pyridazone either fails completely or gives a very small quantity of the desired product. The reactions of this invention have now been demonstrated to proceed through a unique intermediate compound.

The claimed reaction (I→III) can be run in one step by reacting the trihalocarbinol with hydrazine, preferably as hydrazine hydrate and in excess, in an organic solvent in which the reactants are soluble and to which they are chemically inert at elevated temperatures, for example at above 150° preferably from 150°–175°. Of course the solvent must have a boiling point at or above the reaction temperatured at which the process is carried out unless the reaction is carried out in a pressure reactor. At lower temperatures the pyrazoline derivative is formed in substantial amounts along with the desired pyridazinone (III). For example at about 120° only 20–30% of III is obtained but at 165°–170° 60–70% of partially pure product is obtained.

The solvent is preferably ethylene glycol but similar products may be used such as propylene glycol or the common ether (methyl) or ester (acetate) derivatives of such glycols. Other high boiling inert solvents may be used such as water, dimethylsulfoxide, dimethylacetamide or dimethylformamide. The reaction is allowed to go to completion but reaction times of from about 2–25 preferably about 10 to 20 hours at 155°–175° may be used to best advantage.

The reaction gives excellent yields if an inorganic base is present during the reaction such as an alkali metal carbonate, bicarbonate or hydroxide. Most useful are sodium or potassium carbonates and in about two mole equivalent quantities based on the carbinol starting material. The desired product is isolated by methods known to the art as will be apparent from the illustrative examples.

The starting material trihalocarbinol (I) is prepared by reacting the appropriate o-hydroxyacetophenone with chloral, bromal or a reactive derivative thereof such as the hydrate or alcoholate preferably in acetic acid in the presence of the advantageous ammonium acetate. In all the reactions described herein bromal or the tribromocarbinol derivative corresponding to I can be substituted. However chloral is preferred on a cost per gram basis.

For example, the trichlorocarbinal (I) is reacted with an excess of hydrazine hydrate at 90° for one hour. The structure of the intermediate products assigned in the empirical formula $C_{10}H_{12}N_4O_2$ from the analytical data on the parent compound is a hydrazide having the structural formula:

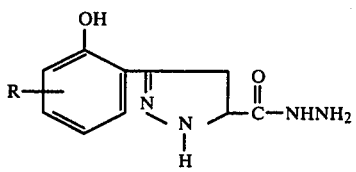

IV in which R is as defined above but is usually hydrogen.

This compound (IV) is then reacted with an excess of hydrazine hydrate in ethylene glycol at 170°–175° for two hours. Working up the resulting product gives a good yield of the desired 6-(2-hydroxyphenyl)-3-pyridazinone (III).

On the other hand reacting trichlorocarbinols without the necessary 2-hydroxy phenyl substitutent yield mostly the expected hydrazone (V):

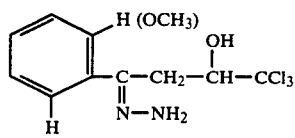

V

The following examples are intended to illustrate the practice of this invention to those skilled in the art. All temperatures are on the Centigrade scale.

EXAMPLE 1

(A) To a solution of o-hydroxyacetophenone (20.4 g, 0.150 m) and ammonium acetate (13 g, 0.17 m) in acetic acid (90 cc) was added chloral hydrate (32 g, 0.19 m) and the solution stirred at 115°–120° overnight. The heat was removed and water (100 cc) was added and the solution stirred while cooling to 15°. A brown-precipitate formed and after 1 hour of stirring it was collected and washed with dilute acetic acid. On drying the light brown solid weighed 33.7 g (79%), m.p. 111°–114°. The thin layer chromatogram (toluene: cyclohexane: acetonitrile; acetic acid—10:10:5:1) on silica gel showed 1 minor and 3 trace components as well as the major component, 1,1,1-trichloro-2-hydroxy-4-(o-hydroxyphenyl)-4-butanone. This is a new compound to the best of our knowledge and is part of this invention.

An identical reaction was run using 90 cc of propionic acid in place of acetic acid. The yield of tan solid was 32.4 g (7%) after drying. A portion of this sample (5 g) was recrystallized from 70% ethanol with a bone carbon treatment with 80% recovery. The thin layer shows essentially 1 spot with a trace at the origin, m.p. 122°–124.5°.

Assay

| Calc'd | Found |
|---|---|
| C 42.36 | 41.77 |
| H 3.20 | 3.26 |
| Cl 37.51 | 38.98 |

Use of catalysts such as pyridine or sodium acetate in place of ammonium acetate resulted in very sluggish reactions with yields only 20–30%.

(B) A solution of o-hydroxyacetophenone (6.8 g, 50 mm), anhydrous chloral 8.25 g (5.5 cc, 56 mm), acetic acid (30 cc) and pyrrolidine (2.7 cc) was stirred and heated 15 hours at 110°. The gas chromatogram indicated the presence of the o-hydroxyacetophenone and the reaction was treated with 1 cc of chloral and 0.2 cc of pyrrolidine and the reaction heated at 120° for 5 hours. On slow addition of water and cooling a dark precipitate formed. The dark product was filtered, washed with water and dried. The product was crystallized from benzene-petroleum ether to give 6.4 g of trichlorocarbinol (45%), m.p. 120°–124°.

EXAMPLE 2

A solution of hydrazine hydrate (4.0 g, 80 mm) in ethylene glycol (50 cc) was stirred at 100°. The trichlorocarbinol (5.0 g, 17.6 mm) was added in one portion and the reaction heated rapidly to 165°–170° (bath temperature). After 16 hours the reaction was cooled to 100° and 3 N hydrochloric acid was added, pH=1.2. Stirring and heating at this temperature was continued for 1.2 hours.

The reaction was poured into ice water and the tan solid collected. The solid was washed free of color with an acetone-ether mixture and dried for 12 hours at 60° in vacuo. Yield 2.26 g (68%) m.p. 280°(d), of impure 6-(2-hydroxyphenyl)-3-(2H)-pyridazinone.

| Calc'd | Found |
|---|---|
| C 63.83 | 62.30 |
| H 4.56 | 4.29 |
| N 14.89 | 17.69 |

The infrared spectrum and NMR were identical to a sample of authentic pyridazinone. However the high pressure liquid chromatogram indicated an impurity of 30–40% was present. The product was purified by crystallization from aqueous dimethylacetamide. Yield 1.0 g (31%).

EXAMPLE 3

A solution of thr trichlorocarbinol (15 g, 0.,053 m) in 98% hydrazine hydrate (90 cc) was heated to 90° for 1 hour. The reaction was cooled to 20° and the solid product filtered and washed with cold aqueous alcohol. The white solid weighed 6.35 (55% based on molecular weight 220); m.p. 194°–198°.

Assay—Mass Spectrum M/e 220.

| Calc'd | Found |
|---|---|
| C 54.54 | 53.97 |
| H 5.49 | 5.51 |
| N 25.44 | 26.41 |

The material contains 1.1% chloride due to ammonium chloride admixture. It reacts with 2 moles of acetone.

To a solution of hydrazine hydrate (2.0 g, 80 mm) in ethylene glycol (20 cc) at 100° was added the above compound (2 g, 9.1 mm). The solution was heated at 5 minutes at 120° then a hot solution of potassium hydroxide (85%, 2.5 g) in ethylene glycol (15 cc) was added. The reaction was stirred and rapidly heated to 170°–175° then stirred at that temperature for 2 hours. The reaction was cooled and poured into water, and the pH was adjusted from 12 to 8.0 with 3 N hydrochloric acid. A thick white precipitate formed and the solution was placed in the icebox overnight. The solid was collected and dried. Yield 0.7 g (3.72 mm, 41%) m.p. 275°–280° (d). The pyridazinone was identical to the product formed in Example 2.

EXAMPLE 4

The deshydroxy trichlorocarbinol (1.22 g, 4.56 mm) was added to a solution of anhydrous hydrazine (0.72 g, 22.8 mm) in ethylene glycol (8 cc) stirred at 95°–100°. After two hours at 110°, the solution was heated to 120° and a hot solution of potassium hydroxide (85%, 1.42 g) in ethylene glycol (8 cc) was added in 2 portions. The reaction was rapidly heated at 170°–175° for 3 hours. On cooling the reaction was poured into cold water and the pH adjusted from 11.4 to 8.0 with 3 N hydrochloric acid. No product could be isolated on standing or cooling this solution. An authentic sample of the desired product was prepared by known methods and shown to be completely insoluble in a water-ethylene glycol solution at pH 8. Using this reference pyridazinone, it was determined that the solution contained 0–5% of the desired product by quantitative thin layer chromatography (Silica Gel G.F., chloroform-methanol 95–5). The chromatogram showed no starting material in a complex mixture.

EXAMPLE 5

Under conditions where the o-hydroxy compound is converted to a $C_{10}H_{12}N_4O_2$ compound, the unsubstituted phenyl compound is simply converted to the corresponding hydrazone V.

A solution of the deshydroxy trichlorocarbinol (5.0 g, 18.7 mm) and 98% hydrazine (1:87 g, 37.4 mm) in ethanol 13 cc) was heated at 70° for 3.5 hours and stirred overnight at room temperature. The reaction (precipitate present) was poured into icewater and the solid yellow, 4.9 g was collected. The product (V) was crystallized from isopropyl alcohol and dried overnight—m.p. 141°; there was a single spot on thin layer chromatogram (silica gel, chloroform-methanol; 90–10).

Assay (V)

| Calc'd | Found |
|---|---|
| C 42.66 | 42.65 |
| H 3.94 | 4.03 |
| N 9.95 | 10.09 |
| Cl 37.77 | 38.01 |

EXAMPLE 6

A solution of o-methoxyacetophenone (22.5 g, 150 m), chloral hydrate (32 g, 193 m), ammonium acetate and propionic acid (90 cc) is heated at 120° for 4 hours. Water (120 cc) was added dropwise and the heating was removed. On cooling, a dark precipitate formed and the product was collected and washed with water. On drying the product weighed 36 g (81%) m.p. 80°–84°. The tan-brown product was recrystallized from benzene-petroleum ether; m.p. 82°–84°.

Assay

| Calc'd | Found |
|---|---|
| C 44.40 | 44.39 |
| H 3.73 | 3.71 |
| Cl 35.74 | 35.80 |

To a solution of hydrazine hydrate (98%, 4.0 g, 80 mm) in 30 cc ethylene glycol at 110° was added the above 1,1,1-trichloro-2-hydroxy-4-(o-methoxyphenyl)-4-butanone (5.24 g, 17.6 mm). After 2 hours at that temperature a hot solution of potassium hydroxide (85%, 5.28 g, 80 mm) in 30 cc of ethylene glycol was added, and the temperature rapidly raised to 170°–175°. After 2 hours the reaction was cooled, and quenched in 150 cc of ice water (pH=11). The pH of the solution was adjusted to 8 but no ppt formed on cooling or standing overnight. The pH was then adjusted to pH−2. No precipitate formed on standing or cooling.

A portion of the above solution was neutralized and extracted with chloroform. Only a small amount of organic soluble material was present.

EXAMPLE 7

The trichlorocarbinol 5.0 g (17.6 mm) was added to a stirred solution of hydrazine hydrate (98–99%, 3.0 g 60 mm) in ethylene glycol (50 cc) at 80°. After 2 hours at 80°, the reaction mixture was removed from the heat and finely powdered potassium carbonate (4.69 g, 34 mm) was added in one portion. No evaluation of gas was noted.

This reaction mixture was placed in an oil bath preheated to 175°–180°; and stirred for 3–4 hours. The reaction was cooled to about 80°–90° and poured into cold water containing 2 cc of 1 N sodium hydroxide.

The pH was adjusted for 8 and the solid was collected and washed with water and acetone and dried. The yield, corrected for purity was 44% of 6-(2-hydroxyphenyl)-3-(2H)-pyridazinone.

EXAMPLE 8

Substituting a molar equivalent quantity of bromal in the procedures of Examples 1(A) and 2 gives 6-(2-hydroxyphenyl)-3-pyridazinone.

What is claimed is:

1. The compound of the formula:

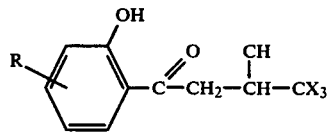

in which X is Cl or Br and R is hydrogen, methyl, ethyl, methoxy, ethoxy, methylthio, ethylthio, halo or trifluromethyl.

2. The compound of claim 1 in which X is Cl.

3. The compound of claims 1 and 2 in which R is hydrogen.

UNITED STATES PATENT AND TRADEMARK OFFICE
CERTIFICATE OF CORRECTION

PATENT NO. : 4,193,941

DATED : March 18, 1980

INVENTOR(S) : Sidney H. Levinson and Wilford L. Mendelson

It is certified that error appears in the above-identified patent and that said Letters Patent are hereby corrected as shown below:

Column 6, line 57;

delete the structure below, ------- and replace with:

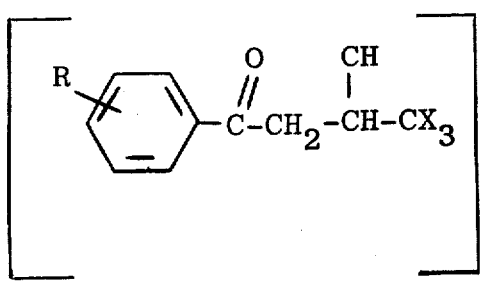 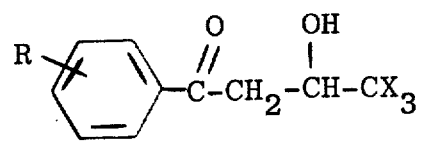

Signed and Sealed this

Twenty-fourth Day of June 1980

[SEAL]

Attest:

Attesting Officer

SIDNEY A. DIAMOND

Commissioner of Patents and Trademarks